US00PP20194P2

(12) United States Plant Patent
Smith

(10) Patent No.: US PP20,194 P2
(45) Date of Patent: Jul. 28, 2009

(54) ***CHRYSANTHEMUM* PLANT NAMED 'YOPENELOPE'**

(50) Latin Name: *Chrysanthemum×morifolium*
Varietal Denomination: Yopenelope

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 12/214,224

(22) Filed: Jun. 16, 2008

(51) Int. Cl.
*A01H 5/00* (2006.01)

(52) U.S. Cl. ..... Plt./290
(58) Field of Classification Search ..... Plt./290
See application file for complete search history.

*Primary Examiner*—Annette H Para
(74) *Attorney, Agent, or Firm*—C. A. Whealy

(57) ABSTRACT

A new and distinct cultivar of *Chrysanthemum* plant named 'Yopenelope', characterized by its compact, upright and mounding plant habit; freely branching habit; uniform and freely flowering habit; decorative-type inflorescences with coral-colored ray florets; and natural season flowering about September 25$^{th}$ in the Northern Hemisphere.

1 Drawing Sheet

Botanical designation: *Chrysanthemum×morifolium.*
Cultivar denomination: 'YOPENELOPE'.

BACKGROUND OF THE INVENTION

The present invention relates to a new and distinct cultivar of *Chrysanthemum* plant, botanically known as *Chrysanthemum×morifolium,* commercially grown as a perennial garden *Chrysanthemum*, and hereinafter referred to by the name 'Yopenelope'.

The objective of the breeding program is to create new perennial garden-type *Chrysanthemum* cultivars having uniformly rounded plant habit, inflorescences with desirable inflorescence forms, attractive floret colors and good garden performance.

The new *Chrysanthemum* originated from a cross-pollination made by the Inventor in December, 2003, in Salinas, Calif. of *Chrysanthemum×morifolium* 'Yojenna', disclosed in U.S. Plant Pat. No. 17,532, as the female, or seed, parent with *Chrysanthemum×morifolium* 'Yoursula', disclosed in U.S. Plant Pat. No. 13,641, as the male, or pollen, parent. The new *Chrysanthemum* was discovered and selected by the Inventor as a single flowering plant within the progeny of the stated cross-pollination in a controlled greenhouse environment in Alva, Fla. in October, 2004.

Asexual reproduction of the new *Chrysanthemum* by vegetative cuttings was first conducted in a controlled greenhouse environment in Alva, Fla. in December, 2004. Asexual reproduction by cuttings has shown that the unique features of this new *Chrysanthemum* are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yopenelope'. These characteristics in combination distinguish 'Yopenelope' as a new and distinct garden *Chrysanthemum* cultivar:

1. Compact, upright and mounded plant habit.
2. Freely branching habit.
3. Uniform and freely flowering habit.
4. Decorative-type inflorescences.
5. Coral-colored ray florets.
6. Natural season flowering occurs about September 25$^{th}$ in the Northern Hemisphere.

In side-by-side comparisons conducted in Alva, Fla., plants of the new *Chrysanthemum* differed from plants of the female parent, 'Yojenna', in the following characteristics:

1. Plants of the new *Chrysanthemum* were not as broad as plants of 'Yojenna'.
2. Plants of the new *Chrysanthemum* flowered more uniformly than plants of 'Yojenna'.
3. Plants of the new *Chrysanthemum* flowered three days later than plants of 'Yojenna' when grown under natural season conditions.
4. Plants of the new *Chrysanthemum* had slightly smaller inflorescences than plants of 'Yojenna'.
5. Ray florets of plants of the new *Chrysanthemum* were lighter in color than ray florets of plants of 'Yojenna'.

In side-by-side comparisons conducted in Alva, Fla., plants of the new *Chrysanthemum* differed from plants of the male parent, 'Yoursula', in the following characteristics:

1. Plants of the new *Chrysanthemum* were more mounded than plants of 'Yoursula'.
2. Plants of the new *Chrysanthemum* had slightly larger inflorescences than plants of 'Yoursula'.
3. Plants of the new v *Chrysanthemum* and 'Yoursula' differed in ray floret color as plants of 'Yoursula' had lavender-colored ray florets.

Plants of the new *Chrysanthemum* can be compared to plants of *Chrysanthemum×morifolium* 'Blushing Emily', disclosed in U.S. Plant Pat. No. 9,074. In side-by-side comparisons conducted in Alva, Fla., plants of the new *Chrysan-*

*themum* differed from plants of 'Blushing Emily' in the following characteristics:

1. Plants of the new *Chrysanthemum* were smaller and more rounded than plants of 'Blushing Emily'.
2. Plants of the new *Chrysanthemum* flowered more uniformly than plants of 'Blushing Emily'.
3. Plants of the new *Chrysanthemum* ad smaller inflorescences than plants of 'Blushing Emily'.

Plants of the new *Chrysanthemum* an be compared to plants of *Chrysanthemum×morifolium* 'Maia', disclosed in U.S. Plant Pat. No. 15,438. In side-by-side comparisons conducted in Alva, Fla., plants of the new *Chrysanthemum* differed from plants of 'Maia' in the following characteristics:

1. Plants of the new *Chrysanthemum* were not as broad as plants of 'Maia'.
2. Plants of the new *Chrysanthemum* flowered one week earlier than plants of 'Maia' when grown under natural season conditions.
3. Plants of the new *Chrysanthemum* had smaller inflorescences than plants of 'Maia'.
4. Inflorescences of plants of the new *Chrysanthemum* lasted two weeks longer than inflorescences of plants of 'Maia'.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the bottom of the sheet comprises a side perspective view of a typical flowering plant of 'Yopenelope' grown in a container.

The photograph at the top of the sheet is a close-up view of typical inflorescences of 'Yopenelope'.

DETAILED BOTANICAL DESCRIPTION

The aforementioned photographs and following observations and measurements describe plants grown in Alva, Fla., during the late spring and summer in a polycarbonate-covered greenhouse and under conditions and practices which approximate those generally used in commercial garden *Chrysanthemum* production. During the production of the plants, day temperatures averaged 32° C. and night temperatures averaged 21° C. Plants were grown in 15-containers under short day/long night conditions. Plants were eleven weeks from planting when the photographs and description were taken. In the following description, color references are made to The Royal Horticultural Society Colour Chart, 1995 Edition, except where general terms of ordinary dictionary significance are used.

Botanical classification: *Chrysanthemum×morifolium* 'Yopenelope'.

Parentage:

*Female, or seed, parent.*—*Chrysanthemum×morifolium,* 'Yojenna', disclosed in U.S. Plant Pat. No. 17,532.

*Male, or pollen, parent.*—*Chrysanthemum×morifolium* 'Yoursula', disclosed in U.S. Plant Pat. No. 13,641.

Propagation:

*Type.*—Terminal vegetative cuttings.

*Time to initiate roots.*—About four days at temperatures of about 21° C.

*Time to produce a rooted young plant.*—About ten to twelve days at temperatures of about 21° C.

*Root description.*—Fine, fibrous; white in color.

*Rooting habit.*—Freely branching.

Plant description:

*Appearance.*—Perennial decorative-type garden *Chrysanthemum*. Compact, upright and mounded plant habit. Freely branching habit, about five lateral branches each with multiple secondary branches; pinching is not required; dense and full plant habit. Strong and vigorous growth habit.

*Plant height.*—About 16.5 cm.

*Plant width.*—About 22 cm.

*Lateral branches.*—Length: About 13.5 cm. Diameter: About 5.5 mm. Internode length: About 1.2 cm. Strength: Strong. Texture: Pubescent; longitudinally ridged. Color: Close to 148A to 148B.

*Leaves.*—Arrangement: Alternate, simple. Length: About 5 cm. Width: About 3.4 cm. Apex: Broadly acute to mucronate. Base: Truncate with attenuate tendencies. Margin: Palmately lobed, sinuses between lateral lobes mostly parallel. Texture, upper and lower surfaces: Pubescence; veins prominent on lower surface. Color: Developing and fully expanded foliage, upper surface: Close to 147A; venation, close to 147B. Developing and fully expanded foliage, lower surface: Close to 147B; venation, close to 147B. Petiole: Length: About 1.2 cm. Diameter: About 2 mm. Texture, upper and lower surfaces: Pubescent. Color, upper and lower surfaces: Close to 147B.

Inflorescence description:

*Appearance.*—Decorative-type inflorescence form with obovate-shaped ray florets. Inflorescences borne on terminals above foliage. Disc and ray florets arranged acropetally on a capitulum. Inflorescences faintly fragrant.

*Flowering response.*—Under natural season conditions, plants flower about September 25$^{th}$ in the Northern Hemisphere.

*Postproduction longevity.*—Inflorescences maintain good color and substance for about four weeks in an outdoor nursery. Inflorescences persistent.

*Quantity of inflorescences.*—About 13 inflorescences develop per lateral branch.

*Inflorescence bud.*—Height: About 1.1 cm. Diameter: About 1.3 cm. Shape: Oblate. Color: Close to 177D.

*Inflorescence size.*—Diameter: About 4.3 cm. Depth (height): About 1.4 cm. Disc diameter: About 3 mm. Receptacle diameter: About 1.6 cm. Receptacle height: About 5 mm. Receptacle color: Close to 148A.

*Ray florets.*—Shape: Obovate. Orientation: Initially upright, then about 30° from vertical. Aspect: Initially incurved, then mostly flat; apices curved upwardly. Length: About 2 cm. Width: About 6 mm. Apex: Obtuse to shallowly emarginate. Base: Acute. Margin: Entire. Texture, upper and lower surfaces: Smooth, glabrous; velvety; longitudinally ribbed. Number of ray florets per inflorescence: About 120 arranged in about ten whorls. Color: When opening, upper surface: Close to 182C. When opening, lower surface: Lighter than 173D. Fully opened, upper surface: Close to 182D; towards the apex on inner ray florets, close to 183B; color becoming closer to 174D with development. Fully opened, lower surface: Close to 159A; color does not fade with development.

*Disc florets.*—Shape: Tubular, elongated. Length: About 2 mm. Diameter: About 1 mm. Number of disc florets per inflorescence: About 15 to 16. Color, immature and mature: Apex: Close to 13A. Midsection: Close to 164B. Base: Close to 157B.

*Phyllaries.*—Number of phyllaries per inflorescence: About 14 arranged in about two or three whorls. Length: About 7 mm. Width: About 2 mm. Shape: Narrowly elliptical. Apex: Acute. Base: Truncate. Texture, upper surface: Smooth, glabrous. Texture, lower surface: Pubescent. Color, upper surface: Close to 144A. Color, lower surface: Close to 148B.

*Peduncles.*—Length, terminal peduncle: About 3.8 cm. Length, fourth peduncle: About 4.2 cm. Diameter, terminal peduncle: About 2 mm. Angle: Mostly upright to 45° from vertical. Strength: Strong. Texture: Pubescent. Color: Close to 148A.

*Reproductive organs.*—Androecium: Not observed. Gynoecium: Pistil length: About 5 mm. Stigma shape: Bi-parted. Stigma color: Close to 2A. Style length: About 3 mm. Style color: Close to 2D. Ovary color: Close to 155A.

*Seed/fruit.*—Seed and fruit production has not been observed.

Disease/pest resistance: Resistance to pathogens and pests common to *Chrysanthemums* has not been observed on plants grown under commercial conditions.

Garden performance: Plants of the new *Chrysanthemum* have demonstrated excellent garden performance and will overwinter in USDA Zones 5 and higher; plants of the new *Chrysanthemum* have been observed to tolerate high temperature of about 38° C.

It is claimed:

1. A new and distinct *Chrysanthemum* plant named 'Yopenelope' as illustrated and described.

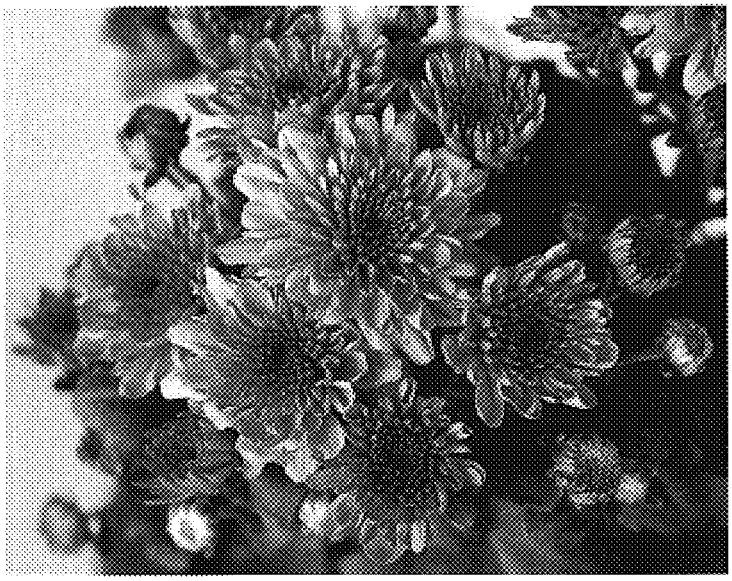
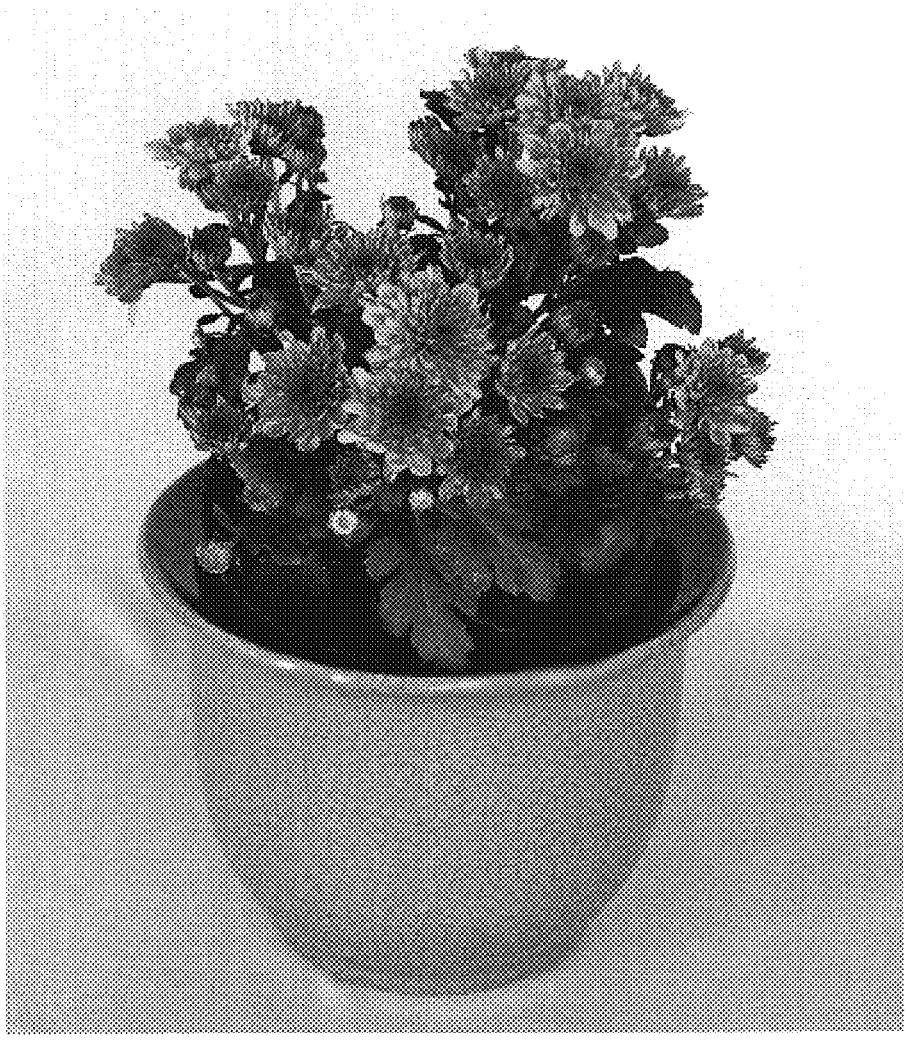

* * * * *